United States Patent [19]

Graham et al.

[11] 4,375,553
[45] Mar. 1, 1983

[54] PROCESS FOR PRODUCING BENZENE CARBOXYLIC ACID SALTS FROM AROMATIC MATERIALS

[75] Inventors: James R. Graham, Fountain Valley, Calif.; John G. Huntington, Broomfield, Colo.

[73] Assignee: Occidental Research Corporation, Irvine, Calif.

[21] Appl. No.: 306,580

[22] Filed: Sep. 28, 1981

[51] Int. Cl.³ .................. C07C 51/16; C07C 51/42
[52] U.S. Cl. ......................... 562/408; 562/407; 562/485; 562/486; 562/494
[58] Field of Search ............... 562/407, 408, 485, 486, 562/494

[56] References Cited

U.S. PATENT DOCUMENTS

| | | |
|---|---|---|
| 2,171,871 | 9/1939 | Walker . |
| 2,176,348 | 10/1939 | Juettner . |
| 2,193,337 | 3/1940 | Leicester . |
| 2,461,740 | 2/1949 | Kiebler . |
| 2,555,410 | 6/1951 | Howard . |
| 2,745,872 | 5/1956 | Carlston et al. . |
| 2,762,840 | 9/1956 | Howard . |
| 2,785,198 | 3/1957 | Grosskinsky et al. . |
| 2,786,074 | 3/1957 | Goren . |
| 2,819,300 | 1/1958 | Grosskinsky et al. . |
| 2,833,816 | 5/1958 | Saffer et al. . |
| 2,927,130 | 3/1960 | Schutt . |
| 2,948,750 | 8/1960 | Blaser et al. . |
| 2,981,751 | 4/1961 | Keith et al. . |
| 3,023,216 | 2/1962 | Blaser et al. . |
| 3,023,217 | 2/1962 | Stein et al. . |
| 3,064,043 | 11/1962 | Taylor et al. . |
| 3,064,046 | 11/1962 | Taylor et al. . |
| 3,115,521 | 12/1963 | Swakon . |
| 3,206,504 | 9/1965 | Christoph, Jr. et al. . |
| 3,215,735 | 11/1965 | Sakurai et al. . |
| 3,259,650 | 7/1966 | Decker et al. . |
| 3,468,943 | 9/1969 | Creighton et al. . |
| 3,529,020 | 9/1970 | Landis et al. . |
| 3,558,458 | 1/1971 | Bloch . |
| 3,579,572 | 5/1971 | Amedjian et al. . |
| 3,629,328 | 12/1971 | Stautzenberger et al. . |
| 3,702,340 | 11/1972 | Selin et al. . |
| 3,709,931 | 1/1973 | Proell et al. . |
| 3,766,258 | 10/1973 | Engelbrecht et al. . |

FOREIGN PATENT DOCUMENTS

| | | |
|---|---|---|
| 498786 | 12/1953 | Canada . |
| 718043 | 9/1965 | Canada . |
| 10-18365 | 12/1935 | Japan . |
| 815835 | 7/1959 | United Kingdom . |

OTHER PUBLICATIONS

Bearse, E. A. et al., "Production of Chemicals by Oxidation of Coal", A Battelle Energy Program Report, Mar. 31, 1975.
Franke, N. W. et al., "Water-Soluble Polycarboxylic Acids by Oxidation of Coal", Ind. and Eng. Chemistry, vol. 44, p. 2791, (1952).
U.S. Bureau of Mines Information Circular No. 8234, pp. 74-98.
Ogata, Yoshiro et al., "The Preparation of Terephthalic Acid from Phthalic or Benzoic Acid", J. Am. Chem. Soc., vol. 79, pp. 6005-6008.
Chin, Yu-Ren, "Terephthalic Acid from Toluene via Dipotassium Terephthalate", Stanford Research Institute Report No. PEP'76-2-3, Feb. 1977, (pp. 1-16).

*Primary Examiner*—Alan Siegel
*Attorney, Agent, or Firm*—Forrest E. Logan

[57] ABSTRACT

This invention relates to a method of producing an aqueous solution which comprises soluble benzene carboxylic acid salts which is substantially free of soluble humic acid salts. A first aqueous solution (22) which comprises soluble humic acid salts and soluble benzene carboxylic acid salts is reacted with carbon dioxide (32) and an inorganic chemical (34) selected from the group consisting of magnesium bicarbonate, magnesium carbonate, a double salt of magnesium carbonate, and mixtures thereof in a mixing zone (30) under conditions operable for converting the soluble humic acid salts to precipitated magnesium humic acid salts while maintaining the soluble benzene carboxylic acid salts in solution. The reacted first aqueous solution (36) is then separated in a separation zone (40) into (i) a second aqueous solution (44) which comprises the soluble benzene carboxylic acid salts and which is at least substantially free of soluble humic acid salts, and (ii) a mixture (42) which comprises precipitated magnesium humic acid salts.

26 Claims, 3 Drawing Figures

PROCESS FOR PRODUCING BENZENE CARBOXYLIC ACID SALTS FROM AROMATIC MATERIALS

TECHNICAL FIELD

The technical field of the invention relates to the production of benzene carboxylic acid salts from aromatic materials. Suitable non-limiting aromatic materials are coal, coal char, coke, chars produced from lignite, pitch, tar, petroleum residium, petroleum, shale oil, and tar sands. The invention is useful for the separation of benzene carboxylic acid salts from an aqueous solution which comprises a mixture of dissolved aromatic carboxylic acid salts.

BACKGROUND ART

U.S. Pat. No. 3,629,328 discloses a method of purifying organic acids such as terephthalic acid by forming a solution of the acid in an aqueous solution of a weak acid salt of magnesium, treating the solution to reduce impurities upon recrystallization of the acid, cooling the solution to recrystallize the acid in a free acid form, and separating the acid from the mother liquor.

U.S. Pat. No. 3,115,521 discloses a process for purifying aromatic acids by treating an aqueous solution of an alkaline salt of an aromatic carboxylic acid with carbon monoxide under pressure. The impurities precipitate, and the solution can be further treated with activated carbon to remove the remaining colored impurities.

U.S. Pat. No. 2,745,872 discloses a method for separating mixtures of salts of terephthalic acid and isophthalic acid by forming a mixture of the salts with a concentrated aqueous solution of an inorganic alkali metal salt, the aqueous solution being insufficient to dissolve all of the mixed alkali phthalic acid salts, and separating a solid phase and a liquid phase from the mixture.

U.S. Pat. No. 3,206,504 discloses a method for separating isophthalic acid from other aromatic carboxylic acids by treating the mixture of acids with reagents to preferentially solubilize the terephthalic acid and monocarboxylic acids present without solubilizing too much of the isophthalic acid, and then separating a solution of the solubilized impurities from the solid bulk of the mass.

Canadian Pat. No. 718,043, discloses a method for separating impurities from naphthalene dicarboxylic acid prepared by the oxidation of dimethylnaphthalene. Impure dinaphthalene carboxylic acid is dissolved in aqueous sodium hydroxide, acidifying the solution to precipitate impurities, separating the impurities, further acidifying the solution to precipitate purer naphthalene dicarboxylic acid and separating the acid.

Canadian Pat. No. 498,786 discloses a process for oxidizing coal at elevated temperature and pressure with an oxygen-containing gas in the presence of an aqueous alkaline solution to produce a solution of alkaline salts of organic acids such as sodium salts. The alkaline solution is then discharged from the reaction vessel and is filtered to remove ash. The alkaline solution is then treated with a mineral acid to free the organic acids from their salts. The organic acids in solution are extracted from the acidified aqueous solution by a solvent such as methyl ethyl ketone.

British Pat. No. 815,835 discloses a process for producing aromatic carboxylic acids, their esters and salts, by reacting an aromatic halogenated hydrocarbon with the formate of an alkali or alkaline earth metal at an elevated temperature or pressure. Instead of using formate directly, the formate may be formed in situ using a compound such as magnesium hydroxide. The reaction may then be extracted with benzene, and the residue treated with water and acidified. The precipitate is the free acid desired.

U.S. Pat. No. 2,785,198 discloses a process for producing polycarboxylic acids from bituminous coal, lignites, peat and the like or their carbonization products such as coal, tar, or pitch by thermal treatment with oxidizing agents such as nitric acid, chromic acid, permanganate, or oxygen or air under super-atmospheric pressure in an alkaline medium. The alkaline medium disclosed is sodium hydroxide. Also disclosed is a process for extracting low molecular weight polycarboxylic acids from the crude oxidation product produced by the thermal oxidation of carbonaceous matter. The oxidation produced is extracted with at least one polar organic solvent for both the monocyclic aromatic and the high molecular weight polycarboxylic acids so as to cause dissolution of the polycarboxylic acids. The solution is treated with water to dissolve the monocyclic acids in the water. The aqueous solution of monocyclic aromatic polycarboxylic acids is separated from the remainder of the mixture, and the monocyclic aromatic polycarboxylic acids are recovered.

The crude oxidation product is subject to an extraction treatment with a polar organic solvent for both the monocyclic aromatic and high molecular weight polycarboxylic acids, and treating the thusly formed solution with water to extract the monocyclic aromatic polycarboxylic acids from the remainder of the mixture.

U.S. Pat. No. 2,193,337 discloses a process for producing organic acids by heating carbonaceous material such as sawdust, wood chips, peat, or coal with oxygen-containing gases at elevated pressures and temperatures in the presence of at least 10 times the weight of the carbonaceous material of water and preferably an oxide or hydroxide of an alkali or alkaline earth metal. Oxalic acid and other organic acids which are formed, such as mellitic and benzoic acid or acetic acid, may be isolated from the resulting reaction mixture as salts of the alkali or alkaline earth metals. The caustic material disclosed is an oxide or hydroxide of an alkali metal or an alkaline earth metal and specifically lime, quick-lime, and caustic soda.

U.S. Pat. No. 2,786,074 discloses a process for making organic acids by oxidizing carbonaceous materials at elevated temperatures and pressures with gaseous oxygen in the presence of an alkaline solution. Alkalis which are suitable for use in a high pressure reactor are specified as sodium hydroxide, potassium hydroxide, and mixtures thereof.

U.S. Pat. No. 2,461,740 discloses a process for oxidizing carbonaceous material to aromatic acids using a two-stage oxidation process.

In the first stage, the carbonaceous material is oxidized to a state where it is soluble in aqueous alkali such, for example, as a solution of sodium hydroxide, potassium hydroxide, sodium carbonate, or potassium carbonate, especially at elevated temperatures.

Any acid or acid anhydride with suitable oxidizing properties which can be regenerated by air and recycled in the process can be employed, for example, sulfur trioxide, oxides of nitrogen, or the acids formed by reaction of these compounds with water. Specifically disclosed are sulfur trioxide, $N_2O_3$, and $N_2O_5$.

In the second stage, U.S. Pat. No. 2,461,740 discloses the use of a high pressure elevated temperature reaction of oxygen gas in aqueous alkali. The aqueous alkali employed is a solution of sodium hydroxide, potassium hydroxide, sodium carbonate, or potassium carbonate.

U.S. Pat. No. 3,023,217 discloses a process for introducing carboxyl groups into aromatic compounds free from carboxyl groups, such as aromatic carbocyclic hydrocarbons and aromatic heterocyclic hydrocarbons. The patent discloses a process for introducing into aromatic carbocyclic or aromatic heterocyclic compounds free from carboxyl groups by reacting such materials in the absence of substantial amounts of oxygen, such as a non-oxidative atmosphere and under anhydrous conditions, with alkali metal salts of aliphatic carboxylic acids at elevated temperatures and pressures in the presence of catalysts. As disclosed in the process, it is necessary to exclude the presence of substantial quantities of oxygen. Examples of aliphatic carboxylic acids which are used in the form of their alkali metal salts, especially their potassium salts, are oxalic acid, malonic acid, maleic acid, and trichloroacetic acid.

Examples of suitable compounds free from carboxyl groups which may be used as starting materials for the process are aromatic carbocyclic compounds free from carboxyl groups such as monocyclic aromatic hydrocarbons such as benzene or its derivatives having saturated alkyl or cycloalkyl substitutes attached thereto, and dicyclic aromatic hydrocarbons such as naphthalenes, diphenyl, and other polycyclic aromatic hydrocarbon compounds. Similarly, aromatic heterocyclic compounds free from carboxyl groups which may be used as starting materials are heterocyclic compounds which contain one or more heteroatoms in the ring and which are designated as having an aromatic character because of their chemical behavior.

U.S. Pat. No. 2,948,750 discloses a process for carboxylating aromatic hydrocarbons by direct introduction of carbon dioxide to produce polycarboxylic acids.

Suitable starting materials which are disclosed are aromatic hydrocarbons, especially benzene but also toluene, xylene, cumene and diisopropyl benzene and other benzenes substituted with saturated or unsaturated alkyl or cycloalkyl radicals, naphthalene, diphenyl, diphenylmethane and other aromatic compounds which may also be substituted with hydrocarbon radicals.

Selective carboxylation is accomplished by heating the starting materials in the presence of an acid-binding agent, and carbon dioxide under anhydrous conditions. Examples of the acid-binding agent are carbonates of alkali metals, especially potassium carbonate, the salts of other weak acids such as bicarbonates, formates, or oxalates. Similarly, the corresponding compounds of other metals are suitable; for example, the carbonates of the alkali earth metals.

U.S. Pat. No. 3,023,216 discloses a method of introducing carboxyl groups into aromatic carbocyclic compounds free from carboxyl groups by reacting these compounds in a non-oxidative atmosphere with alkali metal salts of aromatic carbocyclic or aromatic heterocyclic carboxylic acids.

Suitable compounds which are free from carboxyl groups which may be used as starting compounds in this patent are similar to the starting compounds in U.S. Pat. No. 2,948,750.

U.S. Pat. No. 3,023,216 discloses reacting aromatic carboxylic compounds free from carboxyl groups with aromatic carboxylic acids in the form of their alkali metal salts.

Both U.S. Pat. Nos. 3,023,216 and 2,948,750 require specific chemical compounds as starting materials.

U.S. Pat. No. 2,833,816 discloses a process for oxidizing aromatic compounds using a catalyst comprising a lower aliphatic carboxylate salt of a heavy metal and bromine. Examples of a heavy metal are manganese, cobalt, nickel, chromium, vanadium, molybdenum, tungsten, tin, and cerium.

The metals may be supplied in the form of metal salts; for example such as manganese acetate. The bromine may be supplied as ionic bromine, or other bromine compounds soluble in the reaction medium such as potassium bromate.

Thus, the process requires the conjoint presence of bromine and a heavy metal oxidation catalyst.

The starting material required is an aromatic compound containing one or more aliphatic substituents to produce corresponding aromatic carboxylic acids.

U.S. Pat. No. 3,064,043 discloses a process for oxidizing para-toluic acid or para-formyl toluene to produce terephthalic acid.

U.S. Pat. No. 3,064,046 discloses a process for oxidizing toluic acid or formyl toluene to produce orthophthalic acid or isophthalic acid.

Both U.S. Pat. Nos. 3,064,043 and 3,064,046 require specific starting materials to be oxidized.

U.S. Pat. No. 3,558,458 discloses a process for preparing aromatic acids by treating an alkyl aryl ketone with water at an elevated temperature in the presence of a reaction promoting agent. The reaction promoting agent may comprise an alkaline catalyst, a transition metal salt, or actinic light. Examples of an alkaline catalyst include potassium acetate, lithium acetate, rubidium acetate, and cesium acetate. The process is conducted in water at a temperature of about 200° to 400° C.

The art discloses processes for the alkaline oxidation of coal employing large amounts of chemicals relative to the amount of water soluble coal acid produced, see U.S. Pat. No. 2,786,074 and a report entitled "Production of Chemicals by Oxidation of Coal", Battelle Laboratory, Columbus, Ohio of Mar. 31, 1975.

Recovery of caustic soda and sodium carbonate was disclosed by Industrial and Engineering Chemistry, Volume 44 (1952), at page 2791 in an article entitled "Water-Soluble Polycarboxylic Acids by Oxidation of Coal" beginning at page 2784.

Japanese patent disclosure 18,365 discloses the reclamation of alkali by recrystallization and requires the consumption of one part by weight of the alkali and 1.5 parts of sulfuric acid for each two parts of coal consumed.

Non-alkaline oxidation of coal generally yields about 10 parts by weight of water soluble coal acids based on 100 parts of coal carbon consumed. Alkaline oxidation yields have been about 30 to about 42 parts per 100 parts of coal carbon consumed. Therefore, alkaline oxidation processes are favored because of the higher yield possible.

In systems like HCl/KCl, $H_2SO_4/K_2SO_4$, and $HNO_3/KNO_3$, the salts do not produce an alkali solution by hydrolysis because the acids involved are too strong. These systems over oxidize the coal and therefore result in much lower yield of coal acids.

Another disadvantage of treatment of coals with strong acids is the production of unwanted by-products by chlorination, sulfation, or nitration of the aromatic nuclei of the coal.

Coal acids have been prepared by nitric acid oxidation, U.S. Pat. Nos. 3,468,943; 3,709,931; 2,555,410; in the presence of nitrogen catalyst, U.S. Pat. No. 3,702,340; and oxidation in a non-alkaline aqueous medium, U.S. Pat. No. 3,259,650.

The caustic-oxygen treatment of coal has been described in U.S. Bureau of Mines Information Circular No. 8234 at pages 74 to 98.

In another process, U.S. Pat. No. 3,259,650 discloses the use of a non-alkaline medium and produces lower yields of water soluble coal acids.

U.S. Pat. No. 2,927,130 discloses a process for the recovery of alkalis and terephthalic acid from aqueous solutions containing alkali salts of terephthalic acid. Alkalis of interest are sodium, potassium and ammonium. The patent discloses that dialkali salts of terephthalic acid in aqueous solution can easily be divided into difficulty soluble monoalkali salts and alkali bicarbonate by introducing carbon dioxide into the solution, and that the difficulty soluble monoalkali salts of terephthalic acid can be hydrolyzed with water into free terephthalic acid and dialkali salts of terephthalic acid. The free terephthalic acid separates out as a solid, while the dialkali terephthalate remains in solution.

U.S. Pat. No. 2,819,300 discloses a process for oxidizing carbonaceous material with nitric acid, and then oxidizing the oxidation products produced from the nitric acid-carbonaceous material reaction with sulfuric acid to complete the oxidation to benzene carboxylic acids.

Although oxidation can be carried out in reclaimable acidic media, these processes are not as desirable because of lower yields and unwanted by-products due to chlorination, sulfation, and nitration.

The art discloses a process for preparing terephthalic acid by heating pure potassium phthalate, or pure potassium isophthalate, or pure potassium benzoate in the presence of catalyst such as cadmium, zinc and other metals, as reported in the Journal of American Chemical Society, Volume 79, pages 6005 to 6008.

The art discloses a catalytic process for preparing terephthalic acid from toluene by oxidizing toluene to benzoic acid, reacting the thusly formed benzoic acid with potassium terephthalate in a methathesis reaction to produce terephthalic acid and potassium benzoate, and heating the thusly formed potassium benzoate in the presence of a catalyst to produce potassium terephthalate and benzene by a disproportionation reaction. Terephthalic acid and benzene are recovered and the thus formed potassium terephthalate is recycled to the methathesis reaction. The process is reviewed in Stanford Research Institute Report No. PEP'76-2-3 of February, 1977.

U.S. Pat. No. 3,215,735 discloses a process for treating a solution containing dialkali terephthalate and non-terephthalic acid as impurities with a reagent to adjust the pH of the solution so that terephthalic acid is in a soluble form while essentially all of the non-terephthalic acid is in an insoluble filterable form.

U.S. Pat. No. 3,579,572 discloses a process for the production of terephthalic acid which comprises treating an aqueous lithium or magnesium terephthalate solution with carbon dioxide under pressure, at a temperature between its solidification temperature and 80° C., and separating the terephthalic acid which precipitates.

U.S. Pat. No. 3,766,258 discloses a process for the catalytic carboxylation of an alkali metal aromatic carboxylate to an acid containing at least one more carboxyl group.

U.S. Pat. No. 2,171,871 discloses that alkali metal derivatives of organic acid salts may be reacted with various reagents reactive with alkali metal organic compounds, e.g. carbon dioxide, sulfur dioxide or organic halides, to produce valuable products.

U.S. Pat. No. 2,176,348 discloses a process for preparing mellitic acid by a two-step oxidation of coal. The coal is first treated with a suitable oxidizing acid with or without the presence of a catalyst, followed by oxidation with an oxidizing salt such as alkaline permanganate.

U.S. Pat. No. 2,762,840 discloses that polycarboxy aromatic acids can be prepared by controlled oxidation with oxygen gas of an aqueous, alkaline suspension of bituminous coal.

U.S. Pat. No. 2,981,751 is directed toward a process for the oxidation of substituted aromatic compounds having at least one aliphatic, cycloaliphatic or partially oxidized aliphatic or cycloaliphatic substituent attached to the aromatic nucleus in the presence of an oxygen-containing gas and a calcined solid oxidation catalyst.

The substituted aromatic feed materials disclosed are toluene, butylbenzene, xylene, cumene, durene, dibutylbenzene, acetophenone, propiophenone, benzaldehyde, tolualdehyde, Tetralin, para-xylene, acetophenone, and cumene hydroperoxide. The oxidation is in the presence of a calcined solid oxidation catalyst which is derived by calcining an inorganic base having deposited thereon catalytic amounts of a promoting metal component.

U.S. Pat. No. 3,529,020 discloses a process for oxidizing an organic material in the presence of a heavy metal crystalline aluminosilicate having uniform pores sufficiently large to permit entry of at least a portion of the organic material, and an oxidation initiator which is present in the pores. The heavy metal crystalline aluminosilicate acts as a catalyst.

One embodiment of this invention is a process for producing benzene carboxylic acid salts comprising treating a mixture of an aromatic material, water, a water soluble reagent comprising a Group Ia or IIa metal, the reagent producing an alkaline solution by hydrolysis, and a promoter agent, with oxygen under conditions sufficient to convert at least a portion of the aromatic material to a benzene carboxylic acid salt of the reagent. The promoter having the formula R—X—$CH_2$—R', wherein:

R comprises a radical selected from the group consisting of alkoxy, phenoxy, substituted phenoxy, hydroxyl, carboxyl, aldo, keto, phenyl, substituted phenyl, alkyl, substituted alkyl, and hydrogen;

X comprises a radical, with at least two points of substitution, selected from the group consisting of benzene ring, substituted benzene ring, multi-ring system, substituted multi-ring system, saturated ring, substituted saturated ring, and $(CH_2)_n$, where n is an integer of at least one; and R' comprises a radical selected from the group consisting of hydrogen, alkyl, substituted alkyl, phenyl, substituted phenyl, hydroxyl, carboxyl, aldo, keto, alkoxy, phenoxy, and substituted phenoxy.

The promoter also comprises at least one easily extractable hydrogen, and has the property of increasing the yield of benzene carboxylic acid salt thusly produced from said aromatic material by an amount higher than the conversion of the aromatic material to benzene carboxylic acid in the absence of said promoter.

In another embodiment the promoter agent has the property of increasing the yield of benzene carboxylic acid salts by an amount substantially higher than an amount equivalent to a stoichiometric conversion of the promoter agent to benzene carboxylic acid salt. The thusly formed benzene carboxylic acid salt is then recovered from the mixture or further processed into more valuable products such as by isomerization to terephthalic acid.

SUMMARY AND DISCLOSURE OF THE INVENTION

This invention separates an aqueous solution which comprises soluble benzene carboxylic acid salts, hereinafter referred to as soluble "BCA" salts, from an aqueous solution which comprises soluble humic acid salts and soluble BCA salts. By benzene carboxylic acid or "BCA" we mean herein any one of or any mixture of benzoic; 1,2 benzene dicarboxylic; 1,3 benzene dicarboxylic; 1,4 benzene dicarboxylic; 1,2,3 benzene tricarboxylic; 1,2,4 benzene tricarboxylic; 1,3,5 benzene tricarboxylic; 1,2,3,4 benzene tetracarboxylic; 1,2,3,5 benzene tetracarboxylic; 1,2,4,5 benzene tetracarboxylic; benzene pentacarboxylic; or benzene hexacarboxylic acid. In other words, by benzene carboxylic acid or BCA as used herein and claimed we mean a benzene ring with one or more carboxyl groups attached directly to a ring carbon and containing no other substituted group or groups.

The aromatic material can be coal of any grade such as bituminous, subbituminous or anthracite, peat, lignite, coke, char, petroleum, petroleum fractions such as petroleum residium, tar, pitch, oil shale, oil from oil shale, chars and cokes from lignite, mixtures thereof, and any other material containing or capable of evolving or producing aromatic material, either liquid or solid. Coals, coal char, coke, chars produced from lignite, petroleum residium, tar, pitch and mixtures thereof are preferred aromatic feed material because such material will produce a good yield of BCA salts by this invention.

Bituminous coal is especially preferred because of the very high yield of BCA salts produced by this process. Whereas, anthracitic coals because of their high aromaticity produce a high percentage of polynuclear aromatic acid salts. Similarly, yields from lignites are low because the oxidation of lignite produces little aromatic material, and therefore the yield of BCA salts is low.

In general, the water soluble reagent is such that it produces an alkaline solution by hydrolysis. In general its chemical formula comprises a cation selected from the group consisting of alkali metals, ammonium, and mixtures thereof. Thus, hydrogen is excluded from the group comprising alkali metals. Water soluble reagents which comprise potassium or sodium alkali metals are preferred members of the group because they are more reactive, have a higher rate of reaction in this invention, produce a high yield of BCA salts, and/or are relatively less expensive.

A water soluble reagent such as potassium carbonate, potassium bicarbonate, a double salt of potassium bicarbonate, or mixtures thereof is especially preferred because it gives a high yield of BCA salts in this invention, it is economical and may be regenerated as set forth in the preferred embodiment below. Other examples of water soluble reagents which may be used are potassium carbonate, sodium carbonate, lithium carbonate, potassium acetate, potassium formate, potassium propionate, sodium acetate, sodium formate, sodium propionate, lithium acetate, lithium formate, lithium propionate, etc.

Pure water in the mixture to be oxidized is not required and in fact process water may be used over and over at least in part.

If desired, the addition of a promoter agent to the mixture can be used to increase the yield of BCA salts.

Promoters having the formula $R-X-CH_2-R'$, are especially useful wherein:

R comprises a radical selected from the group consisting of alkoxy, phenoxy, substituted phenoxy, hydroxyl, carboxyl, aldo, keto, phenyl, substituted phenyl, alkyl, substituted alkyl, and hydrogen;

X comprises a radical, with at least two points of substitution, selected from the group consisting of benzene ring, substituted benzene ring, multi-ring system, substituted multi-ring system, saturated ring, substituted saturated ring, and $(CH_2)_n$, where n is an integer of at least one; and R' comprises a radical selected from the group consisting of hydrogen, alkyl, substituted alkyl, phenyl, substituted phenyl, hydroxyl, carboxyl, aldo, keto, alkoxy, phenoxy, and substituted phenoxy.

Preferably, the promoter also comprises at least one easily extractable hydrogen, and has the property of increasing the yield of benzene carboxylic acid salt thusly produced from said aromatic material by an amount higher than the conversion of the aromatic material to benzene carboxylic acid in the absence of said promoter.

While we do not wish to be bound by theory, it is believed that the promoter agent controls the oxidation of the feed aromatic material by providing a free radical which serves as a chain transfer agent for the oxidation reaction, thereby speeding up the rate of oxidation and simultaneously controlling the oxidation process so as to increase the yield of BCA salts while reducing the conversion of the feed aromatic material to carbon dioxide.

It is preferable that the promoter agent be soluble in the alkaline solution used in the oxidation zone. It is especially preferable that the promoter agent be completely soluble in the quantity in which it is used in the oxidation zone. It is also preferred that the promoter agent have a boiling point of about 300° C. or higher in order to prevent appreciable vaporization of the promoter agent in the oxidation zone. It is also preferred that the promoter agent have a plurality of reactive sites, that is, aliphatic groups, alicyclic groups, hydroxyl groups and/or substituted groups such as ether groups, ringed ether groups or aromatic groups in its chemical structure.

It is also preferred that the promoter agent have surfactant properties, be stable in that it has a good shelf life, and be non-toxic for industrial hygiene purposes.

Preferably about 1 to about 10 parts by weight of water per part by weight of feed aromatic material, about 1 to about 10 parts by weight of a water soluble reagent per part by weight of feed aromatic material, and about 0.0001 to about 2 parts by weight of a promoter agent per part by weight of feed aromatic material are used in preparing the slurry. In general, the water soluble reagent comprises a cation selected from the group consisting of alkali metals, ammonium, and mixtures thereof. More than 10 parts promoter can in some embodiments be used if desired but usually such large quantities of promoter are uneconomical. Preferably enough water is used to enable the slurry to be pumped. Preferably enough water soluble reagent is used to supply the stoichiometric requirements of the reaction.

The mixture can be formed in any manner in a mixing zone using mixers suitable for handling slurries containing solids if a solid or solid-like carbonaceous material is used to produce the aromatic carboxylic acid salts and BCA salts, or mixers suitable for handling liquids if liquid aromatic materials are to be used to produce the carboxylic acid salts.

The mixture is removed from the mixing zone and fed to a reaction zone wherein the mixture is reacted with oxygen, or an oxygen-containing gas such as air. The reaction zone and the mixing zone can be, if desired, in the same vessel as in some batch-type processes, or they may be separate vessels as in some continuous processes. However, a continuous process for the oxidation of the aromatic feed material is preferred over a batch system not only because of process efficiency but also because yields appear to be higher.

The mixture is treated with oxygen under conditions sufficient to convert at least a portion of the aromatic material into BCA salts of the reagent. In general, a temperature of about 200° to about 350° C. is required. The pressure in the reaction zone should be sufficient to maintain a liquid state in the reaction zone. Generally this requires a pressure of from about 250 to about 2000 psia and a period of time from about 2 minutes to about 4 hours. Preferred conditions of oxidation are a temperature from about 250° to about 300° C., a pressure from about 1000 to about 1600 psia, and a period of time from about 0.5 to about 2 hours.

Reaction times in the reaction zone depend upon the temperature, degree of agitation, the proportion of feed aromatic material, water, and water soluble reagent, the solid-to-liquid ratio, and the particle size of the solid material.

During oxidation aromatic carboxylic acids are formed which react with the water soluble reagent which comprises a cation selected from the group consisting of alkali metals, ammonium, and mixtures thereof to form aromatic carboxylic acid salts of the cation of the water soluble reagent. The aromatic carboxylic acid salts comprise soluble BCA salts of the cation, soluble humic acid salts of the cation, and soluble non-BCA salts of the cation. By soluble non-BCA salts as used herein is meant those soluble aromatic carboxylic acid salts of the cation which have a lower molecular weight than the soluble humic acid salts excluding the soluble BCA salts.

The oxidation products are separated into (1) an aqueous solution which is substantially free of undissolved solids and which comprises the soluble aromatic carboxylic acid salts of the cation of the reagent, and (2) a mixture which comprises mainly solids which comprise the undissolved solids in the oxidized product mixture. It is the object of this invention to separate the soluble benzene carboxylic acid salts of the cation of the reagent from the soluble humic acid salts of the cation of the reagent. This invention separates from the aqueous solution of soluble aromatic carboxylic acid salts which is substantially free of undissolved solids, an aqueous solution which comprises soluble benzene carboxylic acid salts which is at least substantially free of soluble humic acid salts and undissolved solids. This is accomplished by treating the aqueous solution of soluble aromatic carboxylic acid salts with carbon dioxide and an inorganic chemical selected from the group consisting of magnesium bicarbonate, magnesium carbonate, a double salt of magnesium carbonate, and mixtures thereof under conditions operative for converting at least a major part, and preferably at least substantially all, of the soluble humic acid salts to precipitated magnesium humic acid salts while maintaining at least the major part, and preferably at least substantially all, of the soluble benzene carboxylic acid salts in solution. The treated solution is then separated into a liquid part which comprises at least a major part of the soluble benzene carboxylic acid salts and which is at least substantially free of the soluble humic acid salts and undissolved solids, and a mixture which comprises mainly solids which comprise at least a major part, and preferably at least substantially all, of the precipitated magnesium humic acid salts, and any other undissolved solids in the treated product. This invention, therefore, is useful to separate soluble benzene carboxylic acid salts from an aqueous solution which comprises other soluble aromatic carboxylic acid salts such as soluble humic acid salts. Such a solution containing such mixtures of soluble aromatic carboxylic acid salts can be produced from processes other than solely the aqueous alkaline oxidation of an aromatic material, as described above. Such soluble aromatic carboxylic acid salts can be made to comprise a cation selected from the group consisting of alkali metals, ammonium, and mixtures thereof. In one embodiment of this invention, such soluble aromatic carboxylic acid salts comprise principally soluble potassium benzene carboxylic acid salts. In one embodiment of this invention when such soluble aromatic carboxylic acid salts are produced by the aqueous alkaline oxidation of an aromatic material, the water soluble reagent is a water soluble potassium reagent, and in a preferred embodiment the potassium reagent is selected from the group consisting of potassium carbonate, potassium bicarbonate, and mixtures thereof.

In general, then, this invention is a process for separating an aqueous solution which comprises soluble benzene carboxylic acid salts from an aqueous solution which comprises soluble humic acid salts as well as soluble benzene carboxylic acid salts. The process comprises treating the aqueous solution with carbon dioxide and an inorganic chemical selected from the group consisting of magnesium bicarbonate, magnesium carbonate, a double salt of magnesium carbonate, and mixtures thereof under conditions operative for converting at least a major part of the soluble humic acid salts to precipitated magnesium humic acid salts while maintaining at least the major part of the soluble benzene carboxylic acid salts in solution. The treated aqueous solution is then separated into: (1) a second aqueous solution which comprises at least a major part of the soluble benzene carboxylic acid salts and which is at least substantially free of the soluble humic acid salts and undissolved solids, and (2) a mixture which comprises mainly solids which comprise at least a major part of the precipitated magnesium humic acid salts. Conditions operative for treating the aqueous solution with carbon dioxide and the magnesium inorganic chemical are a temperature from slightly above the melting temperature of the aqueous solution to be treated to about 100° C., a carbon dioxide partial pressure of at least about 1 psi, an amount of magnesium inorganic chemical from about 1 to about 10 percent by weight of the aqueous solution to be treated, and a period of time of treating from about 5 minutes to about 5 hours. Temperatures just above the melting point of the solution to be treated are necessary because the reaction forming the magnesium humates occurs in the liquid state. Temperatures greater than about 100° C., although they can be used, are not desirable because the solubility of the carbon dioxide in the aqueous solution becomes relatively low, and hence lowers the concentration of magnesium bicarbonate formed by its absorption into the solution which in turn slows up the precipitation of magnesium humates. Of course, if the magnesium inorganic chemical is totally magnesium bicarbonate, then little if any carbon dioxide is required since magnesium bicarbonate is readily soluble in the aqueous solutions under the conditions operable for precipitating magnesium humates. In one preferred embodiment, the temperature is from about 10° to about 35° C. Temperatures below about 10° C. are not desirable because the cooling costs for maintaining the lower temperature become expensive. Similarly, temperatures above 35° C. are not desirable because heating costs become more expensive, and also the solubility of carbon dioxide decreases as the temperature increases. Broadly speaking, carbon dioxide partial pressure less than 1 psi are not preferred because the carbon dioxide solubility into the aqueous solution becomes very slow. Thus, higher carbon dioxide partial pressure are preferred. Carbon dioxide partial pressure over about 2,000 psi are not desirable, however, because the capital cost of providing high pressure equipment to effect the process is substantially more expensive than low pressure equipment. However, high carbon dioxide partial pressure does increase the solubility rate of carbon dioxide in the aqueous solution, and hence the rate of formation and precipitation of magnesium humates. Because of these factors, it is preferred to conduct the formation and precipitation of magnesium humates at a carbon dioxide partial pressure from about 50 to about 150 psi. Carbon dioxide partial pressure below about 50 psi result in decreased solubility of the carbon dioxide into the aqueous solution, and hence a slowing up of the formation and precipitation of magnesium humates, while carbon dioxide partial pressures greater than about 150 psi result in higher equipment cost for the process. The period of time of treating with the magnesium reagent and carbon dioxide will vary depending on the temperature, the selection of magnesium reagent, and/or the partial pressure of carbon dioxide. Generally, the period of time for treating is from about 5 minutes to about 5 hours. Treating times less than about 5 minutes probably will not precipitate all the humates unless extremely low temperatures and extremely high carbon dioxide partial pressures are used. Similarly, treating times greater than about 5 hours usually do not improve the precipitation of magnesium humates unless extremely high temperatures and extremely low carbon dioxide partial pressures are used. Therefore, in this invention it is preferred to use a period of time for treating from about 0.5 to about 2 hours. Times less than about 0.5 hours may not precipitate all the humates unless low temperatures and high carbon dioxide partial pressures are used. While treating times greater than about 2 hours usually produce little improvement in magnesium humate formation and precipitation unless high temperatures and low carbon dioxide partial pressures are used.

The ratio of magnesium chemical to soluble humate is from about 0.5 to about 10 when calculated on a magnesium carbonate and average carboxyl group per humate basis. In other words, at least one bicarbonate ion should be provided per humate carboxyl group in order to precipitate all humates. Ratios greater than about 10 are not desirable merely because the cost of the magnesium chemical becomes too expensive. Preferably this ratio is from about 1 to about 4, which provides a stoichiometric amount of bicarbonate to humate carboxyl group of from 2 times to 8 times stoichiometric amount required to precipitate all humates. When the aromatic material is selected from the group consisting of coal, coal char, coke, chars produced from lignite, pitch, tar, petroleum residium, and mixtures thereof, the amount of magnesium inorganic chemical usually required is from about 1 to about 10 percent by weight of the solution of soluble aromatic carboxylic acid salts based on a magnesium carbonate basis for a solution which does not contain undissolved solids. It has been found that such solutions produced by the aqueous alkaline oxidation of coal usually have between about 1 to about 2 percent humates by weight for a solution which does not contain undissolved solids.

In the preferred embodiment of this invention, the BCA's formed during the aqueous alkaline oxidation react with the water reagent to form BCA salts, and carbon dioxide or the volatile acid of the reagent, all of which can be reclaimed by recycling directly or venting the vapor from the reactor and condensing. After treatment with the magnesium inorganic chemical as described above the soluble BCA salts can be separated from the mixture by evaporation and drying or by other means. The separated BCA salts can be recovered or further treated, for example, as by isomerizing to produce terephthalic acid salt which can be further treated for production and recovery of terephthalic acid.

Alternatively, the BCA salts while in solution can be converted to BCA's by treatment of the soluble BCA salt solution with an acid. The BCA's are caused to precipitate at least in part by the aforementioned treatment. The precipitate BCA's can then be recovered from the aqueous slurry.

For example, in one embodiment of this invention, after separating an aqueous solution which comprises at least a major part of the soluble BCA salts and which is at least substantially free of soluble humates, water is removed from the solution in a dewatering zone. In the dewatering zone, an amount of water is removed which is sufficient that upon the addition of "an acid of said reagent" that at least a portion of the BCA salt will be converted to an aromatic carboxylic acid precipitate. The solution will contain the regenerated reagent which can be recycled for further use.

As used above and hereinafter, the expression "an acid of the reagent" means an acid which is formed by the replacement of the Group Ia or IIa metal atom of the water soluble reagent with hydrogen. For example, if the water soluble reagent is potassium acetate then the "acid of the reagent" is acetic acid.

The dewatering zone can be in the same vessel as the reaction zone as in some batch processes, or it can be in a separate vessel as in some continuous processes.

The water from the dewatering zone can be used in the mixing zone to supply at least part of the water requirements for the mixing zone.

The dewatered mixture, i.e., the mixture from the dewatering zone, is then treated in an acidification zone with an acid of the reagent to convert the BCA salt to an aromatic carboxylic acid precipitate and the reagent. For example, potassium terephthalate treated with carbonic acid or with carbon dioxide is converted to potassium hydrogen terephthalic and potassium bicarbonate.

The acidification zone may be in the same vessel as the dewatering zone as in some batch processes, or it can be in a separate acidification vessel as in some continuous processes. Sufficient acid is added in this embodiment to the mixture to effect the conversion of the BCA salts to BCA's and to cause precipitation.

After forming the BCA precipitate, the precipitate is separated from the mixture in a separation zone. Any apparatus capable of separating solids from liquids may be used such as a filter. The separated solid comprises the BCA precipitate.

In one embodiment of the invention, the separated liquid from the separation zone is treated in a regeneration zone to recover the reagent from the liquid. The liquid stream from the acidification zone contains both the reagent and an acid of the reagent. The reagent and the acid of the reagent are separated in a separation zone. The separated reagent can be used for additional treatment of fresh aromatic material in the mixing zone whether the process is batch or continuous. The separated acid of the reagent can be used to acidify additional material in the acidification zone whether the process is batch or continuous.

In another embodiment of this invention, terephthalic acid is produced by drying the BCA salts produced from the feed aromatic material and heating the dry BCA's under isomerization conditions of elevated temperature and pressure to produce terephthalic acid salt. In one embodiment, isomerization is performed without converting the BCA salts to BCA salts of a different alkali metal or ammonium prior to isomerizing the BCA salts. Thus, for example, in this particular embodiment, sodium salts of BCA's are not converted to potassium salts of BCA's prior to isomerization, thereby saving the step of converting sodium BCA salts to potassium BCA salts prior to isomerization and associated cost.

The terephthalic acid salt thusly produced is then converted to a terephthalic acid, and the water soluble reagent comprising said alkali metal or ammonium is regenerated. Terephthalic acid is recovered and the water soluble reagent thusly regenerated is recycled to the oxidation zone to supply a portion of the water soluble reagent required for producing the BCA salts.

The process is especially preferred where the feed aromatic material is coal, the reagent is a potassium carbonate, the promoter agent if used is toluic acid, xylene, trimethylbenzene, tetramethylbenzene, pentamethylbenzene, hexamethylbenzene, 1,2,3,4-tetrahydronaphthalene, an ethoxylated secondary alcohol, or mixtures thereof, and the magnesium inorganic chemical is magnesium carbonate.

BEST MODE FOR CARRYING OUT THE INVENTION

Figure 1:
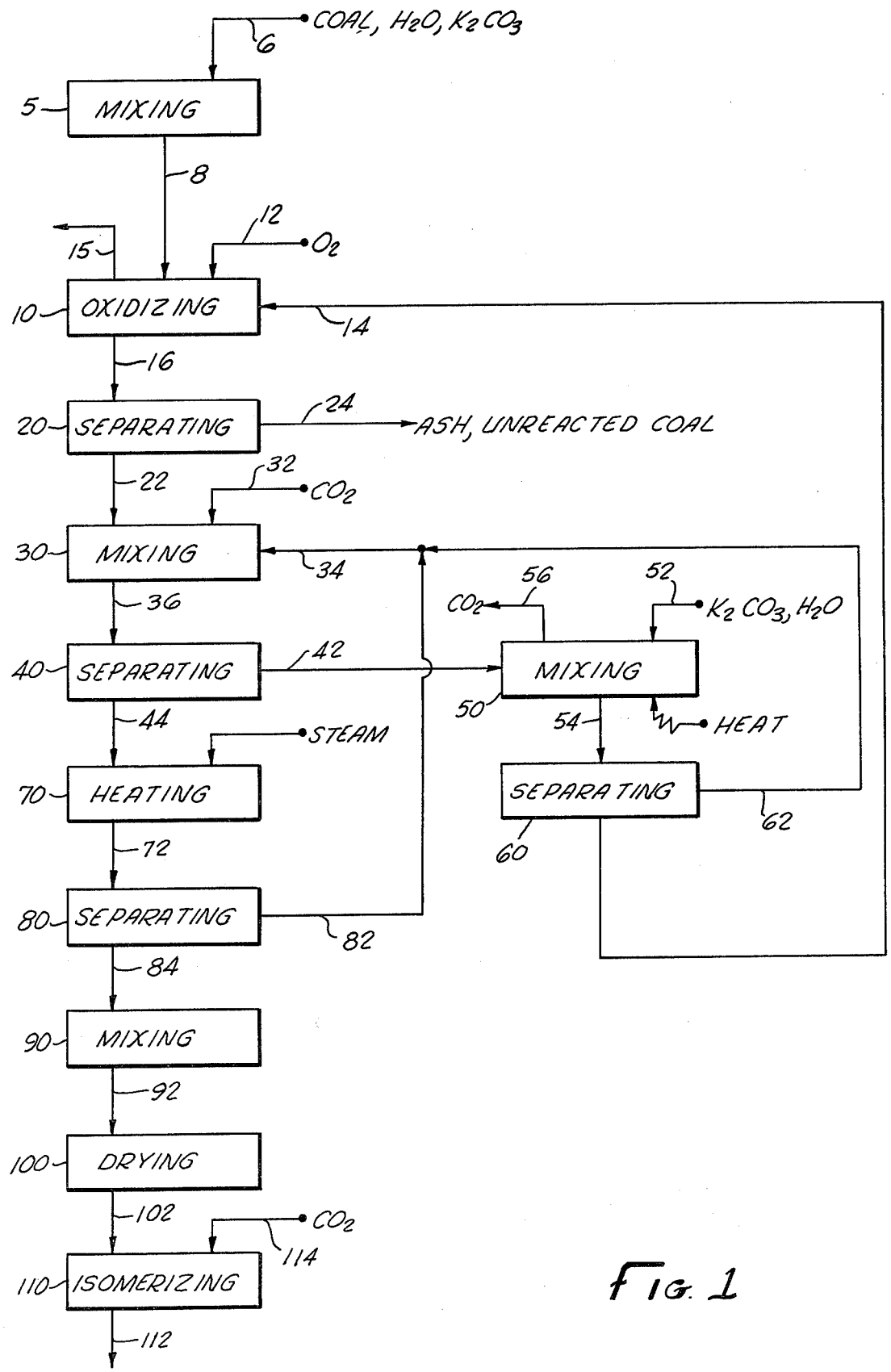
FIG. 1 is a schematic block diagram of a process for producing terephthalic acid from coal.

Referring to FIG. 1, which is a block diagram of a process for producing aromatic carboxylic acid salts, which comprise BCA salts, from coal and the isomerization of the BCA salts to terephthalate, a finely divided coal, preferably bituminous coal, water, potassium reagent, and, if desired, a promoter agent, are introduced into mixing zone 5 through conduit 6. The potassium reagent is selected from the group consisting of potassium carbonate, potassium bicarbonate, or mixtures thereof. About 2 to about 10 parts by weight of water, about 1 to about 10 parts by weight of potassium reagent based on a $K_2CO_3$ basis, and, if desired, about 0.0001 to about 2 parts by weight of a promoter agent per part by weight of coal are introduced into mixing zone 5. Preferably about 4 to about 8 parts by weight of water, about 2 to about 4 parts by weight of potassium reagent, and about 0.05 to about 0.15 parts by weight of an aromatic organic acid promoter agent per part by weight of coal are used in preparing the slurry. In an especially preferred embodiment, about 6 parts by weight of water, about 3 parts by weight of potassium carbonate, and about 0.1 parts of an aromatic organic acid promoter agent, such as toluic acid, are added to mixing zone 5 per part by weight of feed coal introduced into mixing zone 5. Any type of mixer may be used, although a mixer for mixing slurries containing solids is preferred.

After mixing, the mixture is removed from mixer 5 and introduced into oxidizing zone 10, which can comprise an autoclave, through stream 8, along with a recycle stream of soluble potassium humates and soluble potassium non-BCA salts through conduit 14. An oxygen-containing gas such as air or a stream of oxygen is introduced into oxidizing zone 10 through conduit 12. From about 1 parts to about 2.4 parts by weight of oxygen per part by weight of coal is charged to oxidizing zone 10. Preferably about 2 parts by weight of oxygen per part by weight of feed coal is charged to the oxidizing zone. The coal in the alkaline aqueous slurry is oxidized to produce soluble potassium aromatic carboxylic acid salts which comprise soluble potassium BCA salts, soluble potassium non-BCA salts, and soluble potassium humic acid salts. Carbon dioxide and water are also simultaneously produced during the oxidation reaction.

Oxidizing zone 10 is operated at a temperature of about 200° to about 350° C., preferably about 270° C., and at a pressure of about 250 to about 2000 psig, preferably about 1000 to about 1600 psig. Temperatures below about 200° C. are not desirable because the rate of reaction is very slow and temperatures above about 350° C. are not desirable because the formation of carbon dioxide is favored over the formation of BCA salts. Pressures outside this range can be used; however, lower pressures are not desirable because kinetic rates are lower, and higher pressures are not desirable because of the cost of high pressure equipment and compression costs. Of course, the pressure must be equal to or greater than the water vapor pressure in the oxidizer at the oxidation temperature. Preferably the contents of oxidation zone 10 are agitated to increase product yield and to lower reaction time.

Gases comprising carbon dioxide and water vapor are removed from oxidation zone 10 through line 15 and fed into a condenser (not shown) wherein water vapor is condensed and carbonic acid is formed. The condensate and remaining uncondensed gas are removed from the condenser and fed to a separator where the condensate is separated from the remaining gas comprising carbon dioxide in the separator. The gas is removed from the separator through one stream, and the condensate through another stream. Both the gas and the condensate can be used in subsequent steps in the process, if desired.

The aromatic carboxylic acid salts, including the potassium BCA salts, are removed from oxidation zone 10 in stream 16 and fed to separation zone 20 to separate liquids from solids. Separation zone 20 can comprise a filter, such as a precoated revolving drum filter or a vacuum filter. The liquid product containing the dissolved newly formed potassium BCA salts is removed from separator 20 in stream 22. The solids which contain unreacted coal and ash are removed from separation zone 20 in stream 24 and, if desired, recycled, preferably after ash removal, to oxidation zone 10 to undergo further oxidation for the production of additional aromatic carboxylic acid salts including BCA salts.

Separation step 20 is optional and is not needed if the solids in stream 16 will not interfere with a subsequent isomerization step, as described later. With aromatic feed materials such as coals, however, separation step 20 is usually required.

Liquid stream 22 from separator 20 is fed to mixing zone 30 wherein it is mixed with carbon dioxide supplied through conduit 32 and stream 34 which comprises a magnesium inorganic chemical selected from the group consisting of magnesium bicarbonate, magnesium carbonate, a double salt of magnesium carbonate, and mixtures thereof.

In mixing zone 30 the magnesium inorganic chemical either already comprises magnesium bicarbonate or forms magnesium bicarbonate under the conditions of temperature, carbon dioxide partial pressure, and residence time present in the mixing zone. Should the magnesium inorganic chemical be magnesium bicarbonate, then the carbon dioxide partial pressure is of less importance. In any event, magnesium bicarbonate, which is soluble, reacts with the soluble potassium humates and at least a part of the soluble potassium non-BCA salts to produce a magnesium precipitate which comprises magnesium humates and magnesium non-BCA salts. In general, at least a major part, and preferably substantially all of the soluble potassium humates are converted to insoluble magnesium humates, and at least about 15 percent of the soluble potassium non-BCA salts are converted to insoluble magnesium non-BCA salts. Preferably at least about 25 percent of the soluble potassium non-BCA salts are converted to insoluble magnesium non-BCA salts. It is preferred to operate mixing zone 30 at a temperature from about 10° to about 35° C., a carbon dioxide partial pressure from about 50 psi to about 150 psi, while agitating over a period of time from about 0.5 to about 2 hours. Preferably about 1 to about 10 parts by weight of magnesium inorganic chemical is mixed with 100 parts by weight of solution containing the soluble potassium aromatic carboxylic acid salts fed to mixing zone 30 in stream 22, based on a magnesium carbonate basis and a solution which is substantially free of undissolved solids.

After the formation and precipitation of magnesium humates and magnesium non-BCA salts, the mixture is removed from mixing zone 30 in stream 36 and introduced into separation zone 40 wherein the liquids and solids are separated. Separation zone 40 can comprise, for example, a filter.

A mixture which comprises mainly solids which comprise at least a major part, and preferably substantially all, of the precipitated magnesium carboxylic acid salts is removed from separation zone 40 in stream 42 and introduced into mixing zone 50 along with a potassium reagent and water to produce a mixture which comprises soluble potassium humic acid salts and a magnesium precipitate selected from the group consisting of magnesium carbonate, a double salt of magnesium carbonate, and mixtures thereof. The potassium reagent is selected from the group consisting of potassium carbonate, potassium bicarbonate, and mixtures thereof. The mixture in mixing zone 50 is heated under conditions operable for converting insoluble magnesium aromatic carboxylic acid salts contained therein to soluble potassium humates and soluble potassium non-BCA salts. Also formed in mixing zone 50 are potassium carbonate and a magnesium precipitate selected from the group consisting of magnesium carbonate, a double salt of magnesium carbonate, and mixtures thereof. Conditions operable for effecting the formation of soluble potassium humates and soluble potassium non-BCA salts in mixing zone 50 are at a temperature from about 25° to about 150° C., an amount of potassium reagent from about 0.5 parts to about 6 parts by weight per part by weight of magnesium salts fed to mixing zone 50, and an amount of water from about 5 parts to about 50 parts by weight per part by weight of magnesium salts fed to mixing zone 50 in stream 42.

The mixture is removed from mixing zone 50 in stream 54 and introduced into separation zone 60, which can comprise a filter, to separate the solids from the liquids. A stream which comprises mainly solids which comprise the magnesium inorganic precipitate is recycled to mixing zone 30 by way of stream 82 and 34. The liquids removed in stream 14 from separation zone 60 comprise at least a major part of the soluble potassium humic acid salts produced in mixing zone 50. Stream 14 is at least substantially free of undissolved solids and dissolved magnesium aromatic carboxylic acid salts.

Liquid stream 44 from separation zone 40 contains at least a major part of the soluble potassium BCA salts, and no more than about 85 percent of the soluble potassium non-BCA salts produced in oxidation zone 10. Preferably, stream 44 contains no more than about 75 percent of the soluble potassium non-BCA salts produced in oxidation zone 10. Stream 44 also comprises potassium and magnesium bicarbonates.

Stream 44 is fed to heating zone 70 wherein the liquid is heated to convert potassium and magnesium bicarbonates to potassium and magnesium carbonates. Preferably, this conversion is achieved by heating the mixture with steam. However, an inert gas such as nitrogen could be used to speed the removal of carbon dioxide produced in the conversion of the bicarbonates to carbonates. Heating zone 70 is heated to a temperature from about 80° to about 150° C., for a period of time from about 0.1 to about 2 hours. The soluble potassium carbonate and the precipitated magnesium carbonate formed in the heating zone are removed in stream 72 and fed to separating zone 80 which can comprise a filter, to separate liquids and solids. Solids are removed from separating zone 80 in stream 82 which comprises the magnesium carbonate and recycled to mixing zone 30. Liquid stream 84 comprises a solution of potassium BCA salts, potassium non-BCA salts which were not precipitated in separating zone 40, and potassium carbonate.

Stream 84, comprising the soluble potassium BCA salts, is further treated so that the potassium BCA salts can be ultimately isomerized to dipotassium terephthalate. Preferably, stream 84 is fed to mixing zone 90 where it is mixed with an isomerization catalyst. The mixture of soluble BCA salts and isomerization catalyst is removed from mixing zone 90 in stream 92 where it is fed to drying zone 100 which can comprise, for example, a spray dryer. A dried mixture suitable for isomerization is removed from drying zone 100 in stream 102 and fed to isomerization zone 110 where it is isomerized.

In isomerization zone 180, the dry potassium aromatic carboxylic acid salts which comprise potassium BCA salts, are catalytically isomerized at a temperature of from about 400° to about 440° C., at a pressure of from about 5 to about 30 atmospheres, for a period of time of from about 10 to about 100 minutes, to cause isomerization of the dipotassium benzene dicarboxylic acid salts to dipotassium terephthalate. Transcarboxylation reactions can also occur which will contribute to the formation of dipotassium terephthalate.

Preferably, a carbon dioxide atmosphere is maintained in isomerization zone 110. In an especially preferred embodiment, a portion of the carbon dioxide that is produced in oxidation zone 10 is used to create the carbon dioxide atmosphere in isomerization zone 110. If desired, gases other than carbon dioxide can be removed from the gas from oxidation zone 10 before the gas is introduced into isomerization zone 110. In any event, stream 114, which preferably comprises carbon dioxide, must be substantially free of free oxygen and $H_2O$. If desired, any inert atmosphere such as nitrogen may be introduced into the isomerization zone in stream 114 rather than the preferred carbon dioxide.

Examples of catalysts useful for promoting the isomerization are the oxides, carbonates, or halides of zinc or cadmium. Organic salts, particularly carboxylates such as cadmium benzoate, are particularly good catalysts. Cadmium iodide is a preferred catalyst, in concentrations varying from 1 to 15 parts by weight per 100 parts by weight of aromatic carboxylic acid salts. The preferred concentration of cadmium iodide is about 5 parts by weight per 100 parts by weight of the aromatic carboxylic acid salt mixture.

Figure 2:
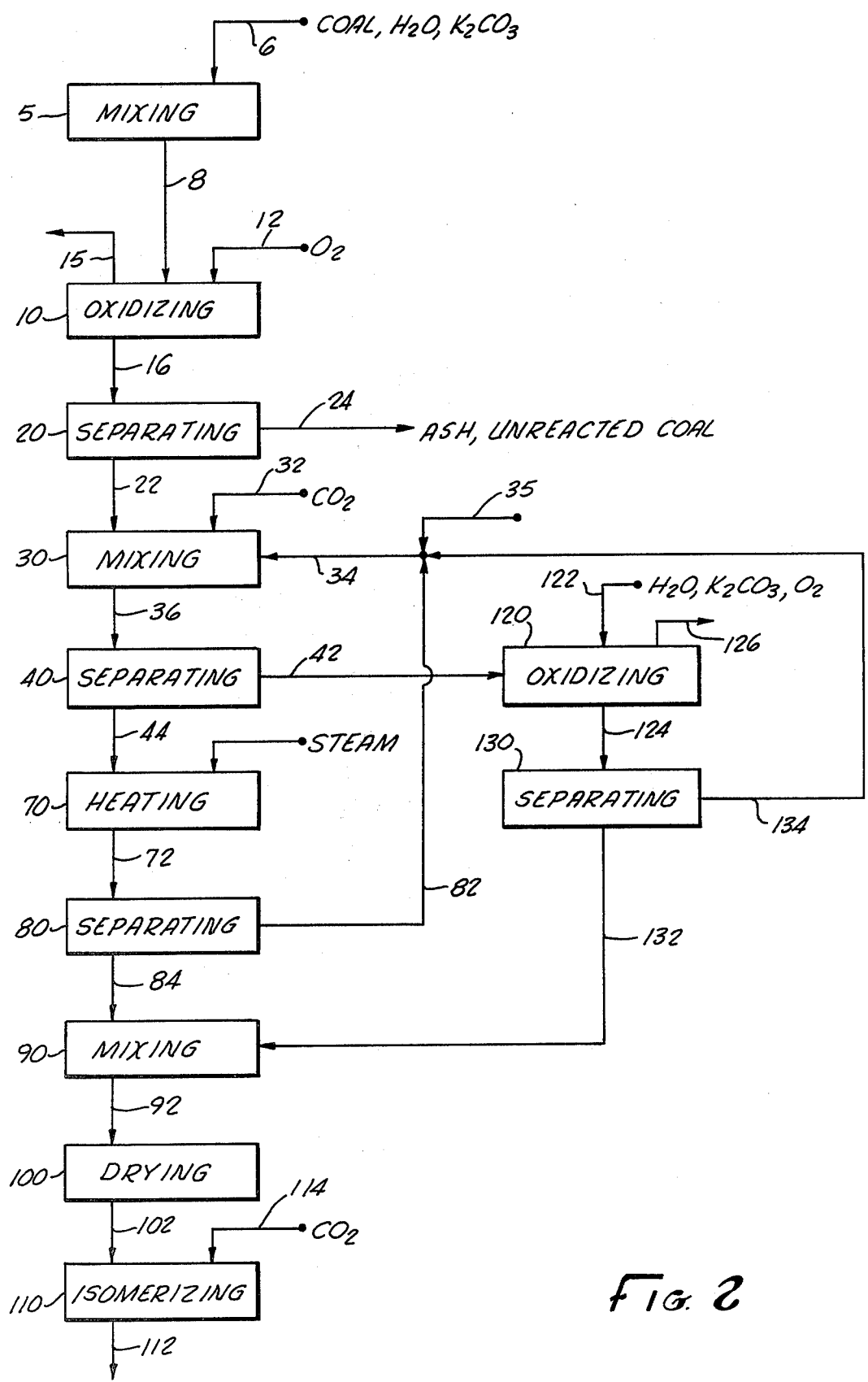
FIG. 2 is a schematic block diagram of a process for producing terephthalic acid from coal which involves secondary oxidation of humates.
Figure 3:
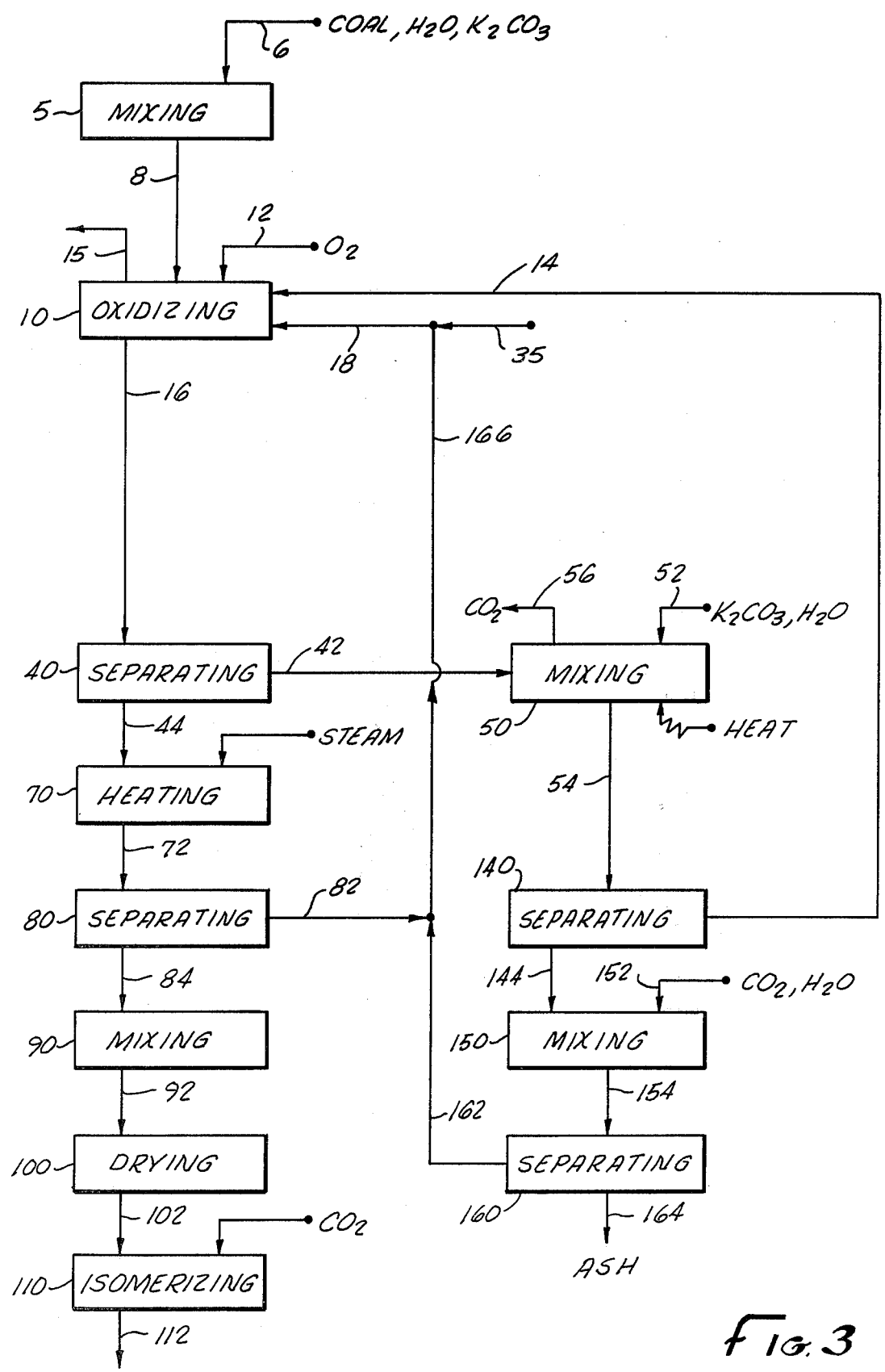
FIG. 3 is a schematic block diagram of a process for producing terephthalic acid from coal which comprises during the oxidation step in situ precipitation of magnesium humates.

In FIG. 2 and FIG. 3, the steps and streams which have the same element number as in FIG. 1 represent identical steps and streams as described above with reference to FIG. 1. FIG. 2 also is a schematic block diagram of an alternative process for producing terephthalic acid from coal which involves a secondary and separate oxidation of humates, rather than the recycle of humates as exemplified in FIG. 1 by stream 14. In the embodiment of this invention as shown by FIG. 2, the solids separated in separating zone 40 which are removed in stream 42, are introduced into second oxidizing zone 120 along with water, a potassium reagent selected from the group consisting of potassium carbonate, potassium bicarbonate, or mixtures thereof, and an oxygen-containing gas such as air, or a stream of oxygen, as shown collectively as stream 122. The precipitated magnesium aromatic carboxylic acid salts which comprise precipitated magnesium humic acid salts, are oxidized under conditions operative to convert the precipitated magnesium aromatic carboxylic acid salts to soluble potassium aromatic carboxylic acid salts which comprise soluble potassium BCA salts. Conditions operative for effecting this oxidation are similar to the conditions in oxidizing zone 10. In particular, the operable conditions are from about 2 to about 10 parts by weight of water, about 1 to about 10 parts by weight of potassium reagent based on a $K_2CO_3$ basis, from about 1 parts to about 2.4 parts by weight of oxygen, and, if desired, about 0.0001 to about 2 parts by weight of a promoter agent per part by weight of precipitated magnesium aromatic carboxylic acid salts fed to oxidizing zone 120. The temperature, pressure, and residence time for oxidizing zone 120 are similar to that of oxidizing zone 10.

The embodiment of this invention in FIG. 2 has the advantage of oxidizing the magnesium aromatic carboxylic acid salts without converting all of the magnesium humates to soluble potassium humates. Stream 124, containing the newly formed soluble potassium aromatic carboxylic acid salts and any remaining precipitated magnesium humic acid salts, is removed from oxidizing zone 120 and fed to separating zone 130, which can comprise a filter, wherein liquids are separated from solids. Liquid stream 132, removed from separating zone 130, can be introduced into mixing zone 90 for further processing along with the soluble potassium BCA salts contained in stream 84. Stream 134, which comprises mainly solids which comprise precipitated magnesium aromatic carboxylic acid salts, can be recycled to secondary mixing zone 30 for further processing until such magnesium aromatic carboxylic acid salts are converted ultimately to soluble potassium aromatic carboxylic acid salts which comprise potassium BCA salts, or carbon dioxide. As in oxidizing zone 10, carbon dioxide is produced in oxidizing zone 120 and removed in gaseous vent stream 126. Stream 126 can be used as a source of carbon dioxide to be introduced into isomerizing zone 110, if desired. The advantage of the FIG. 2 embodiment of this invention over the FIG. 1 embodiment is that all of the precipitated magnesium aromatic carboxylic acid salts do not have to be converted to soluble potassium aromatic carboxylic acid salts before they are subjected to additional oxidation. In FIG. 1, where the recycled aromatic carboxylic acid salts such as humates are recycled to the same oxidation zone as the coal, if magnesium humates rather than potassium humates were recycled, a substantial loss of magnesium from the system would occur as it is removed with the ash and unreacted coal in stream 24. Of course, the magnesium compound could be recovered from the ash but to do so is an additional incurred process expense which it is desirable to avoid. Thus, if the humates are to be directly oxidized in their magnesium form, it is desirable to do so in a zone which is separate from the coal oxidation zone to avoid loss of magnesium from the system or alternatively an expense recovery step.

FIG. 3 represents an alternative embodiment of this invention, shown in block diagram format, for a process for producing terephthalic acid from coal which comprises during the oxidation step the in situ precipitation of magnesium humates. In this embodiment, formation and precipitation of the magnesium humates and magnesium non-BCA salts occur in situ in oxidizing zone 10.

A magnesium inorganic chemical is fed to oxidizing zone 10 in stream 18. At least the major part, and preferably at least substantially all of the magnesium inorganic chemical is supplied by way of recycle stream 166. Make-up magnesium inorganic chemical selected from the group consisting of magnesium bicarbonate, magnesium carbonate, a double salt of magnesium carbonate, and mixtures thereof, can be added as required to the process in stream 35. Stream 35 is employed to replenish magnesium losses which occur in the several embodiments of the process. Separating zone 40 in FIG. 3 not only separates the precipitated magnesium aromatic carboxylic acid salts which comprise magnesium humates and magnesium non-BCA salts, but also ash, any unreacted coal, and any other solids in stream 16. New separating zone 140, mixing zone 150, and separating zone 160 are required in order to remove ash from the system and recover and recycle the magnesium inorganic chemical. In particular, mixing zone 50, which can comprise a stripper in all embodiments, converts the magnesium aromatic carboxylic acid salts to soluble potassium aromatic carboxylic acid salts in the manner similar to that described in FIG. 1 embodiment. Solids and liquids are removed from mixing zone 50 in stream 54 and introduced into separating zone 140, which can comprise a filter, where liquids are separated from solids. Liquid stream 14, which comprises soluble potassium aromatic carboxylic acid salts which comprise potassium humates, no more than about 85 percent of the non-BCA salts and preferably no more than about 75 percent of the non-BCA salts which were produced in oxidizing zone 10, and recycle potassium reagent in the form of potassium carbonate, potassium bicarbonate, or mixtures thereof, is recycled to oxidizing zone 10 in stream 14. Solids are removed from separating zone 140 in stream 144 and fed to mixing zone 150, along with water and carbon dioxide. Stream 144 comprises coal ash, unreacted coal, and a precipitated magnesium inorganic chemical selected from the group consisting of magnesium carbonate, a double salt of magnesium carbonate, and mixtures thereof. In mixing zone 150, the precipitated magnesium inorganic chemical is converted to soluble magnesium bicarbonate which is separated from the remaining solids in the stream in separating zone 160 which can comprise a filter. A magnesium bicarbonate solution is removed from separating zone 160 by way of stream 162 which is then recycled to oxidation zone 10 through means streams 166 and 18. Ash and other solids in stream 154 are removed from the separating zone in stream 164. FIG. 3 embodiment of this invention has the advantage that the coal or other aromatic carbonaceous material is treated with the magnesium inorganic chemical during oxidation of the fed aromatic material to precipitate magnesium humates and magnesium non-BCA salts in situ without the necessity of separation of the ash and unreacted coal immediately after the oxidizing step as provided in oxidizing zone 10.

In general, it is to be understood that streams such as streams 6, 52, 122 and 152, although showing the various reactants entering the various zones in one stream, can be fed to the various zones in separate streams. For example, the oxygen schematically shown entering oxidizing zone 120 of FIG. 2, along with water and the potassium reagent, usually will be fed separately to the oxidizing zone. This and other minor variations through the process can be readily adapted to fit the needs of specific aromatic feed materials to be oxidized, as will be apparent to one skilled in the art. Furthermore, although these embodiments are preferred, it is to be understood that the use of coal as the aromatic feed material and the use of a potassium reagent selected from the group consisting of potassium carbonate, potassium bicarbonate, and mixtures thereof, many other aromatic feed materials can be oxidized by this invention and any alkaline reagent which produces an alkaline solution by hydrolysis and which comprises a cation selected from the group consisting of alkali metals, ammonium, and mixtures thereof, can be used as the water soluble reagent.

EXAMPLE 1

MAGNESIUM TREATMENT ON A TYPICAL COAL OXIDATION PRODUCT 50 ml of an aqueous solution of oxidation product from the caustic oxidation of coal was treated at 25° C., with 2.000 gram of magnesium carbonate and pressurized to 200 psig with $CO_2$. The slurry was stirred for 1 hour, depressurized, and immediately filtered. The precipitate was black due to the magnesium salts of humic acids, and the solution was orange in color, homogeneous, and clear. The amount of soluble solids in the filtrate and the amount of precipitated solids were determined and are reported in Table 1. A second experiment was conducted identical to the first but in which the magnesium carbonate treatment was carried out at 40° C. instead of room temperature. The results of these experiments are also shown in Table 1.

These data show that the procedure precipitates about 30% of the non-BCA coal acids and all of the humic acids as magnesium salts in the coal oxidation product. These precipitated aromatic acids, as their magnesium salts, can be liberated by treating with potassium carbonate, which will precipitate the magnesium as the extremely insoluble carbonate and convert the precipitated magnesium aromatic acid salts into soluble potassium salts.

EXAMPLE 2

OXIDATION USING THE MAGNESIUM PRECIPITATE-RECYCLE

An oxidation experiment using the recycle embodiment of this invention was carried out using a batch coal oxidation unit (BCOU). The heart of the BCOU is a 300 ml Autoclave Engineer Magnadive autoclave. The BCOU is set up so that air can be continuously purged through the batch reactor without water loss from the system. $CO_2$ produced during the oxidation is collected from the off-gas from the reactor and quantitatively determined by weighing.

TABLE 1

| Magnesium Carbonate Treatment of Coal Oxidation Product | | | |
|---|---|---|---|
| Sample | BCA Content (Wt. % of Solids)[1] | Humic Acids (Wt. % of Solids)[1] | Non-BCA (Wt. % of Solids)[1] |
| Oxidation Product; Sample No. A-92 | 4.02 ± 0.4[2] | 6.1 | 11.3 |
| | First Experiment at 25° C. | | |
| Filtrate | 3.71 | nil | 8.12 |
| Precipitate | nil | 6.6 | 3.5 |
| | Second Experiment at 40° C. | | |
| Filtrate | 4.2 | nil | 9.9 |

TABLE 1-continued

Magnesium Carbonate Treatment of Coal Oxidation Product

| Sample | BCA Content (Wt. % of Solids)[1] | Humic Acids (Wt. % of Solids)[1] | Non-BCA (Wt. % of Solids)[1] |
|---|---|---|---|
| Precipitate | nil | 6.7 | 2.7 |

[1]Percentages are based on the weight of soluble solids, calculated as acids, in Sample No. A-92 (first entry).
[2]Average of several analyses.

For this recycle experiment the following feeds were prepared:

Slurry I 15 gram air weathered Pocahontas coal, 45 gram $K_2CO_3$, 1.5 gram toluic acid, 0.73 gram 85% by weight KOH pellets diluted to 500 gram total weight with di-ionized water ($D.I.H_2O$). This slurry was then ball milled for 16 hours prior to use.

Slurry II 45 gram air weathered Pocahontas coal, 45 gram $K_2CO_3$, 4.5 gram m-toluic acid, 2.2 gram 85% by weight KOH pellets diluted to 600 gram total weight with $D.I.H_2O$. This slurry was then ball milled for 16 hours prior to use.

Solution A 93.75 gram of $K_2CO_3$ in 500 gram of $D.I.H_2O$.

Oxidation Cycle 1

150 grams of Slurry I were placed in the BCOU. The BCOU was then heated to 280° C. at a nitrogen pressure of 1300 psig, introduced to the BCOU at a rate of 750 ml/min (STP). Once the BCOU reached equilibrium the $N_2$ flow was switched to an air flow of 750 ml/min. The air flow was continued for 30 minutes after which time the $N_2$ flow was re-established and all the $CO_2$ produced was swept into an ascarite trap for measurement. The reactor was then cooled and the entire reactor product was treated with 4 grams $MgCO_3$ and gaseous $CO_2$. After pH of the solution reached 8 the $CO_2$ treatment was continued for another 45 minutes. The slurry was then filtered, the solid washed with $D.I.H_2O$ and the entire liquid product was freeze-dried and submitted for BCA analysis. The filtered solid thusly produced was treated with 60 grams of Solution A and the mixture heated to boiling for 5 minutes. The resulting slurry was then filtered, the solid washed with water (this solid was acidified, dried and analyzed for carbon hydrogen) and the entire liquid product (filtrate plus washing) was added to 30 grams of Slurry II, diluted to 150 grams, and charged to the BCOU.

Multiple Cycle

In this experiment, the procedure as described above for "Oxidation Cycle 1", was repeated until samples from five cycles were collected. The results are given in Table 2. These results clearly show the recycle embodiment of this invention results in effective separation of humic acid salts. These salts are then recycled for further oxidation. The selectivity of the conversion of coal to BCA salts for this multiple recycle run is significantly improved over a run without recycle of humates. Based on this selectivity the calculated BCA yield for this multiple recycle embodiment was 37 mole %. This improvement is even more pronounced when it is appreciated that the above conditions in the recycle embodiment were not optimized. Considerably better yields can be expected after optimization.

A yield of 32 mole percent was obtained using optimized conditions on a single pass experiment without recycle.

TABLE 2

RESULTS OF 5 CYCLE RECYCLE OXIDATION RUN

Carbon Distribution in Product

| Cycle No. | Grams Coal Carbon Feed to Reactor | Grams Carbon to $CO_2$ | Grams Unreacted Carbon | Grams of Carbon to BCA | Grams of Carbon as Humic & Non-BCA Acids |
|---|---|---|---|---|---|
| 1 | 3.91 | .32 | .98 | .14 | .4 |
| 2 | 1.95 | .23 | .53 | .22 | .7 |
| 3 | 1.95 | .30 | .92 | .18 | .6 |
| 4 | 1.95 | .31 | .19 | .38 | 1.1 |
| 5 | 1.95 | .30 | .16 | .12 | .4 |
| Final Residue | N/A | N/A | N/A | N/A | 3.9[3] |
| TOTAL | 11.71 | 1.76 | 2.78 | 1.04 | 7.1 |

% Coal carbon converted = $\frac{11.71 - 2.78}{11.71} \times 100 = 76\%$

% Coal carbon to $CO_2$ = $\frac{1.76}{11.71 - 2.78} \times 100 = 19.7\%$

% Coal carbon to BCA's = $\frac{1.04}{11.71 - 2.78} \times 100 = 11.6\%$

Calculated BCA yield based on BCA/$CO_2$ selectivity = 37 mole %
[3]by difference
N/A = not applicable

Industrial Applicability

Benzene carboxylic acids can be used as precursors for producing more valuable chemicals such as terephthalic acid. As previously described, dry potassium benzene carboxylic acids can be isomerized to produce terephthalic acid. Terephthalic acid is useful as a precursor for producing polyesters which are useful for producing fibers for the garment industry and plastic containers for liquids and other materials in the bottle or container industry. Benzoic acid is useful as a precursor to valuable chemicals such as phenol. 1,3,5-benzenetricarboxylic acid is useful as a crosslinking agent in the polymer industry. 1,3-benzene dicarboxylic acid has been used as a monomer for polyester. Furthermore, the octyl esters of the latter two acids are useful as plasticisers.

What is claimed is:

1. A process for producing an aqueous solution which comprises soluble benzene carboxylic acid salts which is substantially free of soluble humic acid salts comprising:
    a. reacting a first aqueous solution which comprises soluble humic acid salts and soluble benzene carboxylic acid salts, with carbon dioxide and an inorganic chemical selected from the group consisting of magnesium bicarbonate, magnesium carbonate, a double salt of magnesium carbonate, and mixtures thereof under conditions operable for converting said soluble humic acid salts to precipitated magnesium humic acid salts while maintaining said soluble benzene carboxylic acid salts in solution; and
    b. separating said reacted first aqueous solution into
        i. a second aqueous solution which comprises said soluble benzene carboxylic acid salts and which is at least substantially free of said soluble humic acid salts, and
        ii. a mixture which comprises said precipitated magnesium humic acid salts.

2. A process for separating an aqueous solution which comprises soluble benzene carboxylic acid salts from an aqueous solution which comprises soluble humic acid salts and soluble benzene carboxylic acid salts comprising:
  a. reacting a first aqueous solution which comprises soluble humic acid salts and soluble benzene carboxylic acid salts, with carbon dioxide and an inorganic chemical selected from the group consisting of magnesium bicarbonate, magnesium carbonate, a double salt of magnesium carbonate, and mixtures thereof under conditions operable for converting at least the major part of said soluble humic acid salts to precipitated magnesium humic acid salts while maintaining at least the major part of said soluble benzene carboxylic acid salts in solution; and
  b. separating said reacted first aqueous solution into
    i. a second aqueous solution which comprises at least a major part of said soluble benzene carboxylic acid salts and which is at least substantially free of said soluble humic acid salts and undissolved solids, and
    ii. a mixture which comprises mainly solids which comprise at least a major part of said precipitated magnesium humic acid salts.

3. A process for separating an aqueous solution which comprises soluble benzene carboxylic acid salts from an aqueous solution which comprises soluble humic acid salts and soluble benzene carboxylic acid salts comprising:
  a. reacting a first aqueous solution which comprises soluble aromatic carboxylic acid salts which comprise soluble humic acid salts and soluble benzene carboxylic acid salts, said soluble aromatic carboxylic acid salts comprising a cation selected from the group consisting of alkali metals, ammonium, and mixtures thereof, with carbon dioxide and an inorganic chemical selected from the group consisting of magnesium bicarbonate, magnesium carbonate, a double salt of magnesium carbonate, and mixtures thereof under conditions operable for converting at least the major part of said soluble humic acid salts to precipitated magnesium humic acid salts while maintaining at least the major part of said soluble benzene carboxylic acid salts in solution; and
  b. separating said reacted first aqueous solution into
    i. a second aqueous solution which comprises at least a major part of said soluble benzene carboxylic acid salts and which is at least substantially free of said soluble humic acid salts and undissolved solids, and
    ii. a mixture which comprises mainly solids which comprise at least a major part of said precipitated magnesium humic acid salts.

4. A process for separating an aqueous solution which comprises potassium benzene carboxylic acid salts from an aqueous solution which comprises potassium humic acid salts and potassium benzene carboxylic acid salts comprising:
  a. reacting a first aqueous solution which comprises soluble potassium humic acid salts and soluble potassium benzene carboxylic acid salts, with carbon dioxide and an inorganic chemical selected from the group consisting of magnesium bicarbonate, magnesium carbonate, a double salt of magnesium carbonate, or mixtures thereof under conditions operable for converting at least the major part of said soluble potassium humic acid salts to precipitated magnesium humic acid salts while maintaining at least the major part of said soluble potassium benzene carboxylic acid salts in solution; and
  b. separating said reacted first aqueous solution into
    i. a second aqueous solution which comprises at least a major part of said soluble potassium benzene carboxylic acid salts and which is at least substantially free of said soluble potassium humic acid salts and undissolved solids, and
    ii. a mixture which comprises mainly solids which comprise at least a major part of said precipitated magnesium humic acid salts.

5. A process for producing an aqueous solution which comprises soluble benzene carboxylic acid salts from an aromatic material comprising:
  a. reacting a first mixture which comprises
    i. an aromatic material,
    ii. water, and
    iii. a water soluble reagent which produces an alkaline solution by hydrolysis, said water soluble reagent comprising a cation selected from the group consisting of alkali metals, ammonium, and mixtures thereof,
    with oxygen under conditions operable to convert said aromatic material to soluble humic acid salts of said cation and soluble benzene carboxylic acid salts of said cation;
  b. separating from said reacted first mixture a first aqueous solution which is at least substantially free of undissolved solids, and which comprises at least a major part of said soluble humic acid salts of said cation and said soluble benzene carboxylic acids salts of said cation;
  c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble humic acid salts of said cation to precipitated magnesium humic acid salts while maintaining at least the major part of said soluble benzene carboxylic acid salts of said cation in solution; and
  d. separating said reacted first aqueous solution into
    i. a second aqueous solution which comprises at least a major part of said soluble benzene carboxylic acid salts of said cation and which is at least substantially free of said soluble humic acid salts of said cation and undissolved solids, and
    ii. a second mixture which comprises at least a major part of said precipitated magnesium humic acid salts.

6. A process for producing an aqueous solution which comprises soluble potassium benzene carboxylic acid salts from an aromatic material comprising:
  a. reacting a first mixture which comprises
    i. an aromatic material,
    ii. water, and
    iii. a water soluble potassium reagent which produces
      an alkaline solution by hydrolysis, with oxygen under conditions operable to convert said aromatic material to soluble potassium humic acid salts and soluble potassium benzene carboxylic acid salts;
  b. separating from said reacted first mixture a first aqueous solution which is at least substantially free of undissolved solids, and which comprises at least a major part of said soluble potassium humic acid salts and said soluble potassium benzene carboxylic acid salts;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble potassium humic acid salts to precipitated magnesium humic acid salts while maintaining at least the major part of said soluble potassium benzene carboxylic acid salts in solution; and d. separating said reacted first aqueous solution into
   i. a second aqueous solution which comprises at least a major part of said soluble potassium benzene carboxylic acid salts which is at least substantially free of said soluble potassium humic acid salts and undissolved solids, and
   ii. a second mixture which comprises at least a major part of said precipitated magnesium humic acid salts.

7. A process for producing an aqueous solution which comprises soluble potassium benzene carboxylic acid salts from an aromatic material comprising:

a. reacting a first mixture which comprises
   i. an aromatic material,
   ii. water, and
   iii. a potassium reagent selected from the group consisting of potassium carbonate, potassium bicarbonate, and mixtures thereof,
   with oxygen under conditions operable to convert said aromatic material to soluble potassium humic acid salts and soluble potassium benzene carboxylic acid salts;

b. separating from said reacted first mixture a first aqueous solution which is at least substantially free of undissolved solids, and which comprises at least a major part of said soluble potassium humic acid salts and said soluble potassium benzene carboxylic acid salts;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble potassium humic acid salts to precipitated magnesium humic acid salts while maintaining at least the major part of said soluble potassium benzene carboxylic acid salts in solution; and d. separating said reacted first aqueous solution into
   i. a second aqueous solution which comprises at least a major part of said soluble potassium benzene carboxylic acid salts and which is at least substantially free of said soluble potassium humic acid salts and undissolved solids, and
   ii. a second mixture which comprises at least a major part of said precipitated magnesium humic acid salts.

8. A process for producing an aqueous solution which comprises soluble benzene carboxylic acid salts from an aromatic material comprising:

a. reacting in an oxidation zone a first mixture which comprises
   i. an aromatic material,
   ii. water,
   iii. a water soluble reagent which produces an alkaline solution by hydrolysis, said water soluble reagent comprising a cation selected from the group consisting of alkali metals, ammonium, and mixtures thereof, and
   iv. a recycled aqueous solution which comprises soluble humic acid salts of said cation, with oxygen under conditions operable to convert said aromatic material to soluble humic acid salts of said cation and soluble benzene carboxylic acid salts of said cation;

b. separating from said reacted first mixture a first aqueous solution which is at least substantially free of undissolved solids, and which comprises at least a major part of said soluble humic acid salts of said cation and said soluble benzene carboxylic acid salts of said cation;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble humic acid salts of said cation to precipitated magnesium humic acid salts while maintaining at least the major part of said soluble benzene carboxylic acid salts of said cation in solution;

d. separating said reacted first aqueous solution into
   i. a second aqueous solution which comprises at least a major part of said soluble benzene carboxylic acid salts of said cation and which is at least substantially free of said soluble humic acid salts of said cation and undissolved solids, and
   ii. a second mixture which comprises at least a major part of said precipitated magnesium humic acid salts;

e. mixing and heating said second mixture separated in step (d) with said water souble reagent and water to produce a third mixture which comprises soluble humic acid salts of said cation and a magnesium precipitate selected from the group consisting of magnesium carbonate, a double salt of magnesium carbonate, and mixtures thereof;

f. separating said third mixture into
   i. a third aqueous solution which comprises at least a major part of said soluble humic acid salts of said cation produced in step (e) and which is at least substantially free of undissolved solids and dissolved magnesium salts, and
   ii. a fourth mixture which comprises at least a major part of said magnesium precipitate; and g. recycling said separated third aqueous solution from step (f) to said oxidation zone as said recycled aqueous solution which comprises said soluble humic acid salts of said cation.

9. A process for producing an aqueous solution which comprises soluble potassium benzene carboxylic acid salts from an aromatic material comprising:

a. reacting in an oxidation zone a first mixture which comprises
   i. an aromatic material,
   ii. water,
   iii. a water soluble potassium reagent which produces an alkaline solution by hydrolysis, and
   iv. a recycled aqueous solution which comprises soluble potassium humic acid salts, with oxygen under conditions operable to convert said aromatic material to soluble potassium humic acid salts and soluble potassium benzene carboxylic acid salts;

b. separating from said reacted first mixture a first aqueous solution which is at least substantially free of undissolved solids, and which comprises said soluble potassium humic acid salts and said soluble potassium benzene carboxylic acid salts;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble potassium humic acid salts to precipitated magnesium humic acid salts while maintaining at least the major part of said soluble potassium benzene carboxylic acid salts in solution;

d. separating said reacted first aqueous solution into
  i. a second aqueous solution which comprises at least a major part of said soluble potassium benzene carboxylic acid salts and which is at least substantially free of said soluble potassium humic acid salts and undissolved solids, and
  ii. a second mixture which comprises at least a major part of said precipitated magnesium humic acid salts;

e. mixing and heating said second mixture separated in step (d) with said water soluble potassium reagent and water to produce a third mixture which comprises soluble potassium humic acid salts and a magnesium precipitate selected from the group consisting of magnesium carbonate, a double salt of magnesium carbonate, and mixtures thereof;

f. separating said third mixture into
  i. a third aqueous solution which comprises at least a major part of said soluble potassium humic acid salts produced in step (e) and which is at least substantially free of undissolved solids and dissolved magnesium salts, and
  ii. a fourth mixture which comprises at least a major part of said magnesium precipitate; and g. recycling said separated third aqueous solution from step (f) to said oxidation zone as said recycled aqueous solution which comprises said soluble potassium humic acid salts.

10. The process of claim 9 wherein said water soluble potassium reagent is selected from the group consisting of potassium carbonate, potassium bicarbonate, and mixtures thereof.

11. A process for producing an aqueous solution which comprises soluble benzene carboxylic acid salts from an aromatic material comprising:

a. reacting a first mixture which comprises
  i. an aromatic material,
  ii. water, and
  iii. a water soluble reagent which produces an alkaline solution by hydrolysis, said water soluble reagent comprising a cation selected from the group consisting of alkali metals, ammonium, and mixtures thereof,
    with oxygen under conditions operable to convert said aromatic material to soluble humic acid salts of said cation and soluble benzene carboxylic acid salts of said cation;

b. separating from said reacted first mixture a first aqueous solution which is at least substantially free of undissolved solids, and which comprises at least a major part of said soluble humic acid salts of said cation and said soluble benzene carboxylic acid salts of said cation;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble humic acid salts of said cation to precipitated magnesium humic acid salts while maintaining at least the major part of said soluble benzene carboxylic acid salts of said cation in solution;

d. separating said reacted first aqueous solution into
  i. a second aqueous solution which comprises at least a major part of said soluble benzene carboxylic acid salts of said cation and which is at least substantially free of said soluble humic acid salts of said cation and undissolved solids, and
  ii. a second mixture which comprises mainly solids which comprise at least a major part of said precipitated magnesium humic acid salts;

e. reacting a third mixture which comprises
  i. said separated second mixture from step (d),
  ii. water, and
  iii. said water soluble reagent
    with oxygen under conditions operable to convert said precipitated magnesium humic acid salts to soluble benzene carboxylic acid salts of said cation; and f. separating from said reacted third mixture an aqueous solution which comprises said soluble benzene carboxylic acid salts of said cation produced in step (e).

12. A process for producing an aqueous solution which comprises soluble potassium benzene carboxylic acid salts from an aromatic material comprising:

a. reacting a first mixture which comprises
  i. an aromatic material,
  ii. water, and
  iii. a water soluble potassium reagent which produces an alkaline solution by hydrolysis,
    with oxygen under conditions operable to convert said aromatic material to soluble potassium humic acid salts and soluble potassium benzene carboxylic acid salts;

b. separating from said reacted first mixture a first aqueous solution which is at least substantially free of undissolved solids, and which comprises at least a major part of said soluble potassium humic acid salts and said soluble potassium benzene carboxylic acid salts;

c. reacting said first aqueous solution with carbon dioxide and an inorganic chemical selected from the group consisting of magnesium bicarbonate, magnesium carbonate, a double salt of magnesium carbonate, and mixtures thereof under conditions operable for converting at least the major part of said soluble potassium humic acid salts to precipitated magnesium humic acid salts while maintaining at least the major part of said soluble potassium benzene carboxylic acid salts in solution;

d. separating said reacted first aqueous solution into
  i. a second aqueous solution which comprises at least a major part of said soluble potassium benzene carboxylic acid salts and which is at least substantially free of said soluble potassium humic acid salts and undissolved solids, and
  ii. a second mixture which comprises mainly solids which comprise at least a major part of said precipitated magnesium humic acid salts;

e. reacting a third mixture which comprises
   i. said separated second mixture from step (d),
   ii. water, and
   iii. said water soluble potassium reagent
      with oxygen under conditions operable to convert said precipitated magnesium humic acid salts to soluble potassium benzene carboxylic acid salts; and
f. separating from said reacted third mixture an aqueous solution which comprises said soluble potassium benzene carboxylic acid salts produced in step (e).

13. The process of claim 12 wherein said water soluble potassium reagent is selected from the group consisting of potassium carbonate, potassium bicarbonate, and mixtures thereof.

14. A process for producing an aqueous solution which comprises soluble benzene carboxylic acid salts from an aromatic material comprising:
   a. reacting a first mixture which comprises
      i. an aromatic material,
      ii. water,
      iii. a water soluble reagent which produces an alkaline solution by hydrolysis, said water soluble reagent comprising a cation selected from the group consisting of alkali metals, ammonium, and mixtures thereof, and
      iv. an inorganic chemical selected from the group consisting of magnesium bicarbonate, magnesium carbonate, a double salt of magnesium carbonate, and mixtures thereof,
      with oxygen under conditions operable to convert said aromatic material to soluble benzene carboxylic acid salts of said cation and precipitated magnesium humic acid salts; and
   b. separating said reacted first mixture from step (a) into
      i. a first aqueous solution which comprises at least a major part of said soluble benzene carboxylic acid salts of said cation, and which is at least substantially free of dissolved potassium humic acid salts, said precipitated magnesium humic acid salts, and undissolved solids, and
      ii. a mixture which comprises mainly solids which comprise at least a major part of said precipitated magnesium humic acid salts and undissolved solids which were present in said treated mixture from step (a).

15. A process for producing an aqueous solution which comprises soluble potassium benzene carboxylic acid salts from an aromatic material comprising:
   a. reacting a first mixture which comprises
      i. an aromatic material,
      ii. water,
      iii. a water soluble potassium reagent which produces an alkaline solution by hydrolysis, and
      iv. an inorganic chemical selected from the group consisting of magnesium bicarbonate, magnesium carbonate, a double salt of magnesium carbonate, and mixtures thereof,
      with oxygen under conditions operable to convert said aromatic material to soluble potassium benzene carboxylic acid salts and precipitated magnesium humic acid salts; and
   b. separating said reacted first mixture from step (a) into
      i. a first aqueous solution which comprises at least a major part of said soluble potassium benzene carboxylic acid salts, and which is at least substantially free of dissolved potassium humic acid salts, said precipitated magnesium humic acid salts, and undissolved solids, and
      ii. a mixture which comprises mainly solids which comprise at least a major part of said precipitated magnesium humic acid salts and undissolved solids which were present in said treated mixture from step (a).

16. The process of claim 15 wherein said water soluble potassium reagent is selected from the group consisting of potassium carbonate, potassium bicarbonate, and mixtures thereof.

17. The process of claim 1, 2, 3, 4, 5, 6, 7, 8, 9, 10, 11, 12, 13, 14, 15 or 16 wherein said aromatic material is selected from the group consisting of coal, coal char, coke, chars produced from lignite, pitch, tar, petroleum residium, and mixtures thereof.

18. The process of claim 1, 2, 3 or 4 wherein said conditions operable for said reacting of said first aqueous solution are
   i. a temperature from above the melting temperature of said first aqueous solution to about 100° C.,
   ii. a carbon dioxide partial pressure of at least about 1 psi,
   iii. an amount of said inorganic chemical from about 1 to about 10 percent by weight of said first aqueous solution, and
   iv. a period of time from about 5 minutes to about 5 hours.

19. The process of claim 18 wherein said temperature is from about 10° to about 35° C., said carbon dioxide partial pressure is from about 50 to about 150 psi, and said period of time is from about 30 minutes to about 2 hours.

20. The process of claim 5, 6, 7, 8, 9, 10, 11, 12 or 13 wherein said conditions operable for said reacting of said first aqueous solution are
   i. a temperature from above the melting temperature of said first aqueous solution to about 100° C.,
   ii. a carbon dioxide partial pressure of at least about 1 psi,
   iii. an amount of said inorganic chemical from about 1 to about 10 percent by weight of said first aqueous solution, and
   iv. a period of time from about 5 minutes to about 5 hours.

21. The process of claim 20 wherein said temperature is from about 10° to about 35° C., said carbon dioxide partial pressure is from about 50 to about 150 psi, and said period of time is from about 30 minutes to about 2 hours.

22. The process of claim 20 wherein said conditions operable for said reacting of said first mixture are
   i. a temperature from about 240° to about 320° C.,
   ii. a pressure from about 500 to about 2000 psia, and
   iii. a period of time from about 10 minutes to about 4 hours.

23. The process of claim 14, 15 or 16 wherein said conditions operable for said reacting of said first mixture are
   i. a temperature from about 240° to about 320° C.,
   ii. a pressure from about 500 to about 2000 psia, and
   iii. a period of time from about 10 minutes to about 4 hours.

24. A process for producing an aqueous solution which comprises soluble benzene carboxylic acid salts from an aromatic material comprising:

a. reacting in an oxidation zone a first mixture which comprises
  i. an aromatic material,
  ii. water,
  iii. a water soluble reagent which produces an alkaline solution by hydrolysis, said water soluble reagent comprising a cation selected from the group consisting of alkali metals, ammonium, and mixtures thereof,
  iv. an inorganic chemical selected from the group consisting of magnesium bicarbonate, magnesium carbonate, a double salt of magnesium carbonate, and mixtures thereof, and
  v. a recycled stream which comprises soluble humic acid salts of said cation,
  with oxygen under conditions operable to convert said aromatic material to soluble benzene carboxylic acid salts of said cation and precipitated magnesium humic acid salts;
b. separating said reacted first mixture from said oxidation zone into
  i. a first aqueous solution which comprises at least a major part of said soluble benzene carboxylic acid salts of said cation, and which is at least substantially free of dissolved potassium humic acid salts, said precipitated magnesium humic acid salts, and undissolved solids, and
  ii. a second mixture which comprises mainly solids which comprise at least a major part of said precipitated magnesium humic acid salts and undissolved solids which were present in said reaction mixture from said oxidation zone;
c. reacting said second mixture with said water soluble reagent to convert said precipitated magnesium humic acid salts to soluble humic acid salts of said cation;
d. separating said reacted second mixture into
  i. a second aqueous solution which comprises at least a major part of said soluble humic acid salts, and
  ii. a third mixture which comprises mainly solids which were present in said reacted second mixture; and
e. recycling said second aqueous solution which comprises said soluble humic acid salts to said oxidation zone as said recycled stream.

25. A process for producing an aqueous solution which comprises soluble potassium benzene carboxylic acid salts from an aromatic material comprising:
  a. reacting in an oxidation zone a first mixture which comprises
    i. an aromatic material,
    ii. water,
    iii. a water soluble potassium reagent which produces an alkaline solution by hydrolysis,
    iv. an inorganic chemical selected from the group consisting of magnesium bicarbonate, magnesium carbonate, a double salt of magnesium carbonate, and mixtures thereof, and
    v. a recycled stream which comprises soluble potassium humic acid salts,
    with oxygen under conditions operable to convert said aromatic material to soluble potassium benzene carboxylic acid salts and precipitated magnesium humic acid salts;
  b. separating said reacted first mixture from said oxidation zone into
    i. a first aqueous solution which comprises at least a major part of said soluble potassium benzene carboxylic acid salts, and which is at least substantially free of dissolved potassium humic acid salts, said precipitated magnesium humic acid salts, and undissolved solids, and
    ii. a second mixture which comprises mainly solids which comprise at least a major part of said precipitated magnesium humic acid salts and undissolved solids which were present in said reacted mixture from said oxidation zone;
  c. reacting said second mixture with said water soluble potassium reagent to convert said precipitated magnesium humic acid salts to soluble potassium humic acid salts;
  d. separating said reacted second mixture into
    i. a second aqueous solution which comprises at least a major part of said soluble potassium humic acid salts, and
    ii. a third mixture which comprises mainly solids which were present in said reacted second mixture; and
  e. recycling said second aqueous solution which comprises said soluble potassium humic acid salts to said oxidation zone as said recycled stream.

26. The process of claim 25 wherein said water soluble potassium reagent is selected from the group consisting of potassium carbonate, potassium bicarbonate, and mixtures thereof.

* * * * *